(12) United States Patent
Aramata et al.

(10) Patent No.: US 7,128,731 B2
(45) Date of Patent: Oct. 31, 2006

(54) SYRINGE-TYPE CONTAINER FOR LIQUID MEDICINE

(75) Inventors: Masafumi Aramata, Osaka (JP); Hideki Yagi, Osaka (JP); Hitoshi Futagawa, Osaka (JP); Satoru Igarashi, Osaka (JP)

(73) Assignee: Nipro Corporation, Osaka-fu (JP)

( * ) Notice: Subject to any disclaimer, the term of this patent is extended or adjusted under 35 U.S.C. 154(b) by 21 days.

(21) Appl. No.: 10/319,638

(22) Filed: Dec. 16, 2002

(65) Prior Publication Data

US 2003/0125671 A1    Jul. 3, 2003

(30) Foreign Application Priority Data

Dec. 28, 2001    (JP) .............................. 2001-399027

(51) Int. Cl.
*A61M 5/00*    (2006.01)
(52) U.S. Cl. ...................................... 604/187; 604/110
(58) Field of Classification Search ................ 604/187, 604/411, 537, 68, 82, 110, 188, 181
See application file for complete search history.

(56) References Cited

U.S. PATENT DOCUMENTS

| | | | | |
|---|---|---|---|---|
| 3,559,645 | A | * | 2/1971 | Schaller ...................... 604/192 |
| 4,743,243 | A | | 5/1988 | Vaillancourt |
| 5,584,819 | A | | 12/1996 | Kopfer |
| 6,729,370 | B1 | * | 5/2004 | Norton et al. .............. 141/329 |

FOREIGN PATENT DOCUMENTS

EP    0 499 481 A1    8/1992

\* cited by examiner

*Primary Examiner*—Kevin C. Sirmons
*Assistant Examiner*—Laura C. Schell
(74) *Attorney, Agent, or Firm*—Birch, Stewart, Kolasch & Birch, LLP (57) ABSTRACT

A syringe-type container for liquid medicine which includes a barrel provided with an easily breakable piercing needle at a distal end of a needle-connecting portion thereof; a gasket inserted and held in the barrel; and a guide means fitted on the barrel from the distal side wherein. The syringe-type container is so constructed that turning of the guide means relative to the barrel breaks off the piercing needle from the needle-connecting portion.

6 Claims, 8 Drawing Sheets

SYRINGE-TYPE CONTAINER FOR LIQUID MEDICINE

This nonprovisional application claims priority under 35 U.S.C. § 119(a) on Patent Application No. 2001-399027 filed in JAPAN on Dec. 28, 2001, which is herein incorporated by reference.

FIELD OF THE INVENTION

The present invention relates to a syringe-type container for liquid medicine suitable for use as a so-called prefilled-syringe, i.e., syringe previously filled with a liquid medicine.

BACKGROUND OF THE INVENTION

Certain drugs change their nature or deteriorate in quality when stored in the form of a liquid medicine, and accordingly they are stored in a drug container such as vial in the form of a solid, for example a powder medicine or a freeze-dried medicine. Such solid medicines are mixed with a solution injected into the vial with a syringe just before use to reconstitute the liquid medicine in the vial, and the resultant liquid medicine is then withdrawn into a syringe and injected into a patient. For example, a solid medicine prefilled in a vial is reconstructed by withdrawing a solution from an ample or a vial into a syringe (or fitting a needle for dissolution on a prefilled-syringe containing a solution prefilled therein), causing the needle to penetrate into the rubber stopper of the vial and ultimately into the vial, injecting the solution in the syringe into the vial to reconstitute a liquid medicine by mixing the solution with the solid medicine, and then withdrawing the resultant liquid medicine from the vial into the same syringe.

In the conventional method using a syringe, it is required to use a metal needle for reconstituting of a liquid medicine. Thus, there is a fear of injuring a user with the needle. Also, there is the possibility of coring when the needle is caused to penetrate into the rubber stopper at an angle with respect to the top plane of the stopper.

SUMMARY OF THE INVENTION

Thus, the present invention has been made in view of the above circumstances and is intended to provide a syringe-type container for liquid medicine, which makes it possible to prepare the liquid medicine without causing any injury to the user and coring of the rubber stopper.

The above object of the present invention is achieved by breakably fitting the distal end of a syringe with a piercing needle for dissolution, and providing a means for breaking the piercing needle including guide means for guiding the vial.

According to the present invention, there is provided a syringe-type container for liquid medicine, including:

a barrel having a needle-connecting portion and an easily breakable hollow piercing needle coaxially joined to the distal end of the needle-connecting portion;

a liquid-tight gasket slidably inserted into the barrel through the proximal end thereof; and a hollow guide means fitted at the distal side of said barrel onto the needle-connecting portion thereof to guide a mouth of a vial toward the needle-connecting portion;

wherein said piercing needle is adapted to be broken off from the needle-connecting portion when the guide means is turned with respect to said the barrel.

The guide means may include a fitting portion for connection to the needle-connecting portion, and a guide portion into which the mouth of the vial can be slidably inserted. In this case, the piercing needle is provided at a portion adjacent to the needle-connecting portion with an engaging portion for engagement with the fitting portion of the guide means, and the fitting portion is provided with an engaging means for engagement with the engaging portion. The engaging portion is so designed as to have a shape associate with that of the engaging means. For example, when the engaging portion is made into a shape with a regular polygonal cross section, the engaging means, i.e., the lumen of the fitting portion corresponding to the engaging portion, is made into a shape complementary to that of the engaging portion. Thus, when the engaging portion is provided with at least one longitudinal rib, the fitting portion may be provided with at least one longitudinal groove which engages with the at least one longitudinal rib, or at least one longitudinal rib is adapted to be engaged with said at least one longitudinal rib of said engaging portion when said guide means is turned around the piercing needle. The syringe-type container for the liquid medicine may be a so-called "prefilled syringe", i.e., a syringe previously filled with a liquid medicine.

The above and other objects and features of the present invention will become clear from the following description taken in conjunction with the preferred embodiments thereof with reference to the accompanying drawings throughout which like parts are designated by like reference numerals.

BRIEF DESCRIPTION OF THE DRAWINGS

The present invention will become more fully understood from the detailed description given hereinbelow and the accompanying drawings which are given by way of illustration only, and thus are not limitative of the present invention, and wherein;

FIG. 3(a) is an enlarged section view taken along a line X—X in FIG. 2, FIG. 3(b) is another enlarged section view taken along a line X—X in FIG. 2.

FIG. 4(a) is an enlarged plan view illustrating one form of the guide means, FIG. 4(b) is an enlarged plan view illustrating a modified form of the guide means, and FIG. 4(c) is an enlarged plan view illustrating another modified form of the guild means;

FIG. 5(a) is an enlarged section view taken along lines Y—Y in FIG. 4(a), FIG. 5(b) is an enlarged section view taken along lines Y—Y in FIG. 4(b), FIG. 5(c) is an enlarged section view taken along lines Y—Y in FIG. 4(c);

FIG. 6(a) is an enlarged section view taken along a line Z—Z in FIG. 5(a), FIG. 6(b) is an enlarged section view taken along a line Z—Z in FIG. 5(b), FIG. 6(c) is an enlarged section view taken along a line Z—Z in FIG. 5(c)

DETAILED DESCRIPTION OF THE PREFERRED EMBODIMENTS

Figure 1:
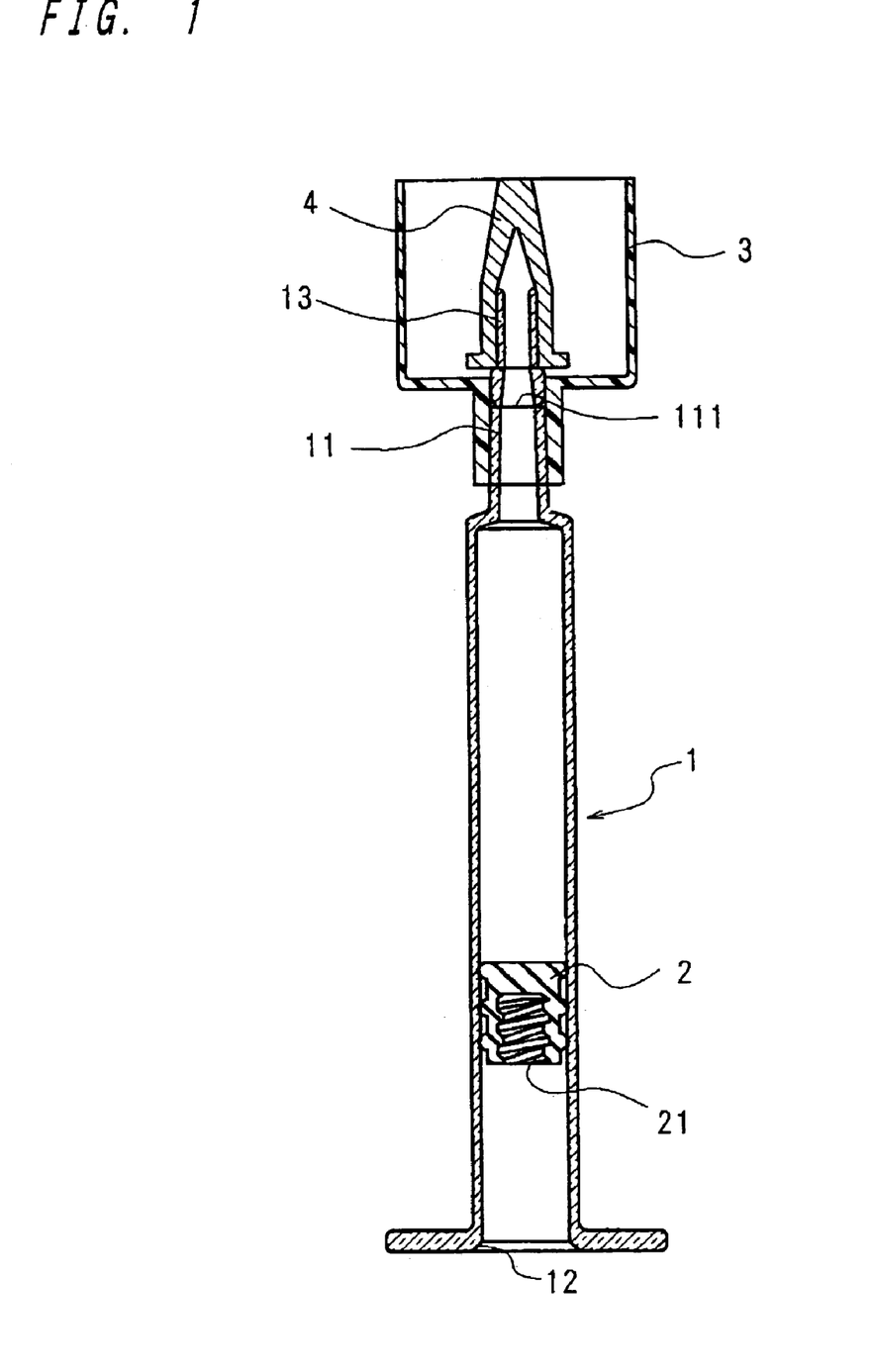
FIG. 1 is a longitudinal section of a syringe-type container for liquid medicine, illustrating one embodiment of the present invention.

As illustrated in FIG. 1, a syringe-type container for liquid medicine according to the present invention includes a barrel 1 having a needle-connecting portion 11 disposed at a distal side thereof and provided with an easily breakable piercing needle 13 at the distal end 111 of the needle-connecting portion 11 thereof; a gasket 2 inserted and held in the barrel 1; and a guide means 3 fitted on the barrel 1 at the distal side thereof. The syringe-type container is so constructed that turning of the guide means 3 relative to the barrel 1 breaks off the piercing needle 13 from the needle-connecting portion 11.

Figure 2:
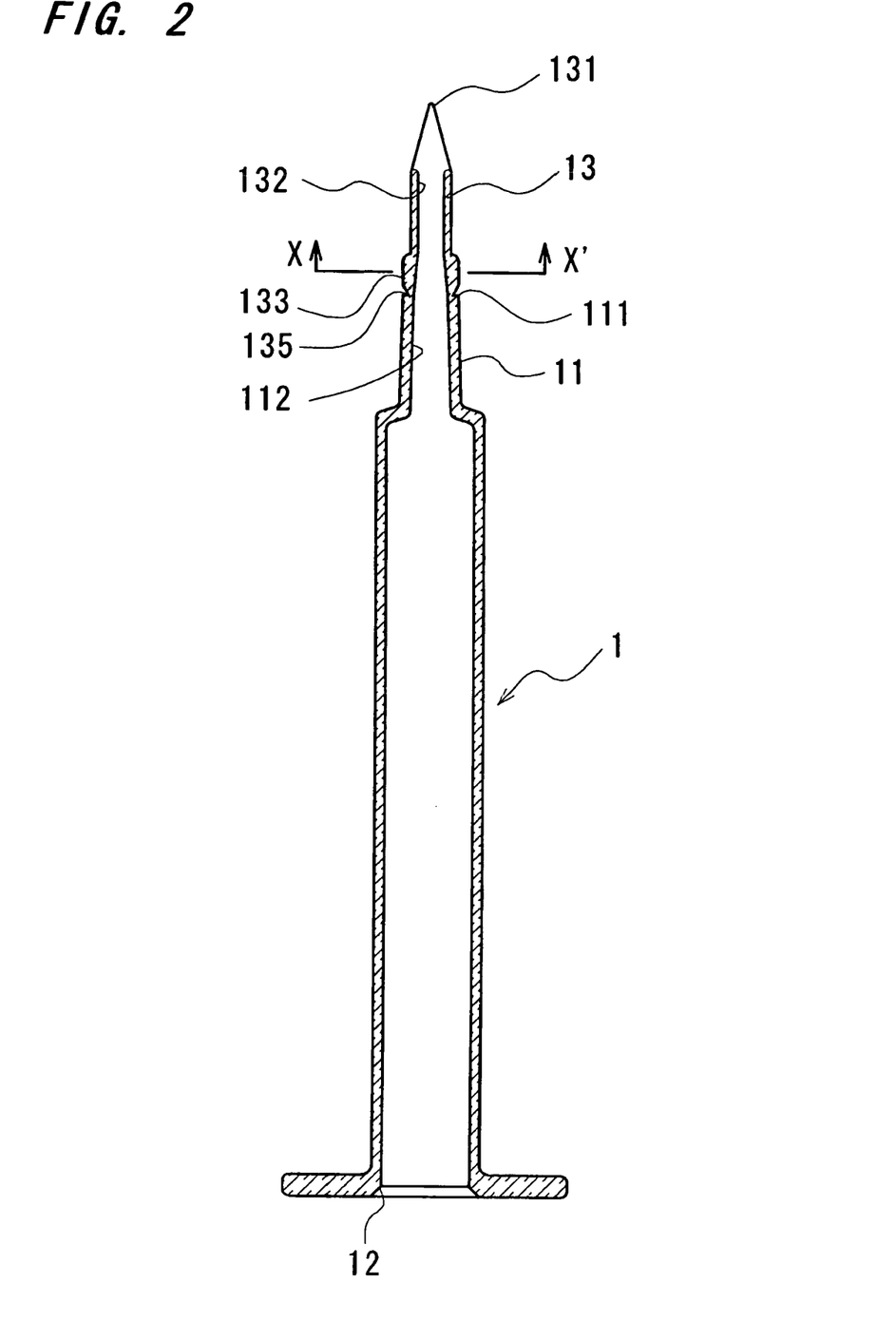
FIG. 2 is a longitudinal sectional of a container body shown in FIG. 1.

The barrel 1 is a cylindrical member generally made of polypropylene, polyethylene or the like. As illustrated in FIG. 2, the piercing needle 13 is coaxially and easily breakably joined to the distal end 111 of the needle-connecting portion 11 to which an injection needle (designated by 7 in FIG. 8) is connected at the time of injection.

Figure 3:
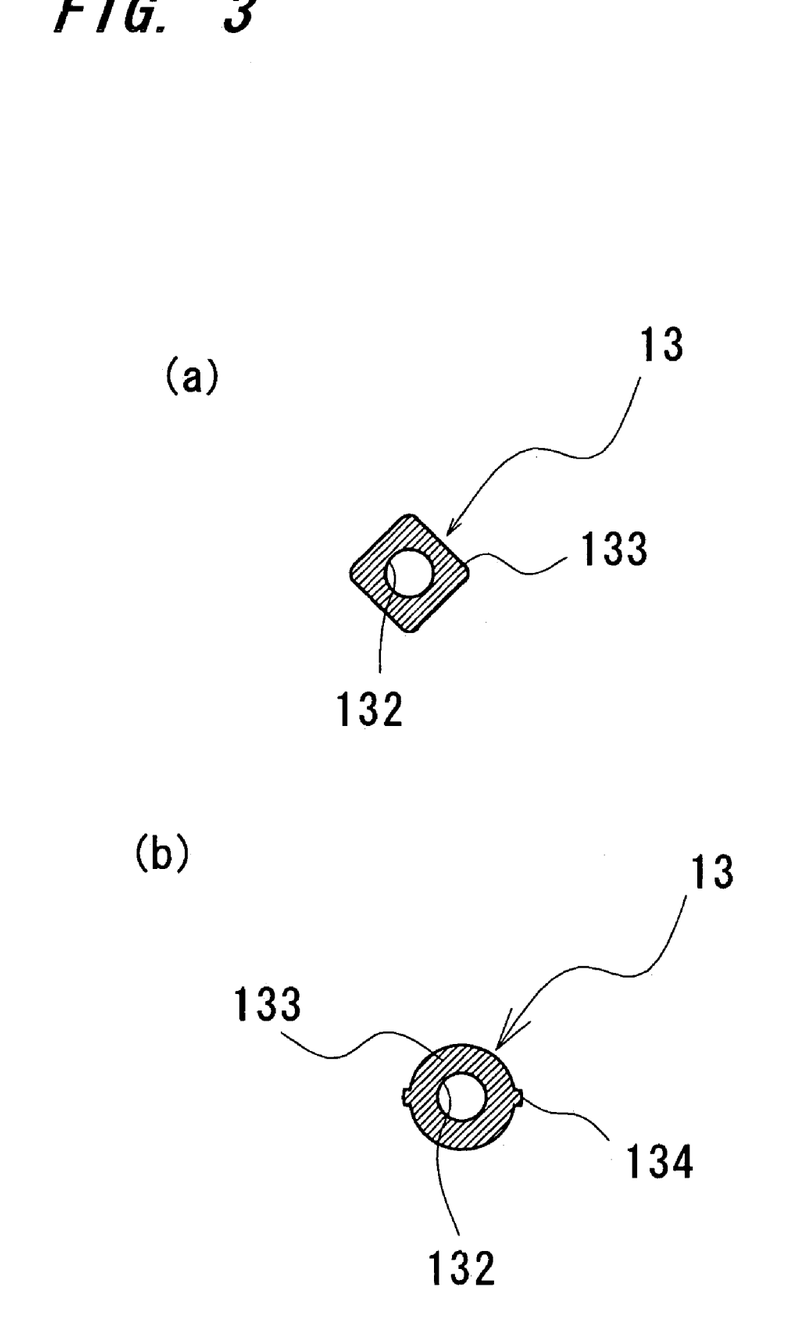
FIG. 3 shows enlarged section views of the container body shown in FIG. 1.
Figure 8:
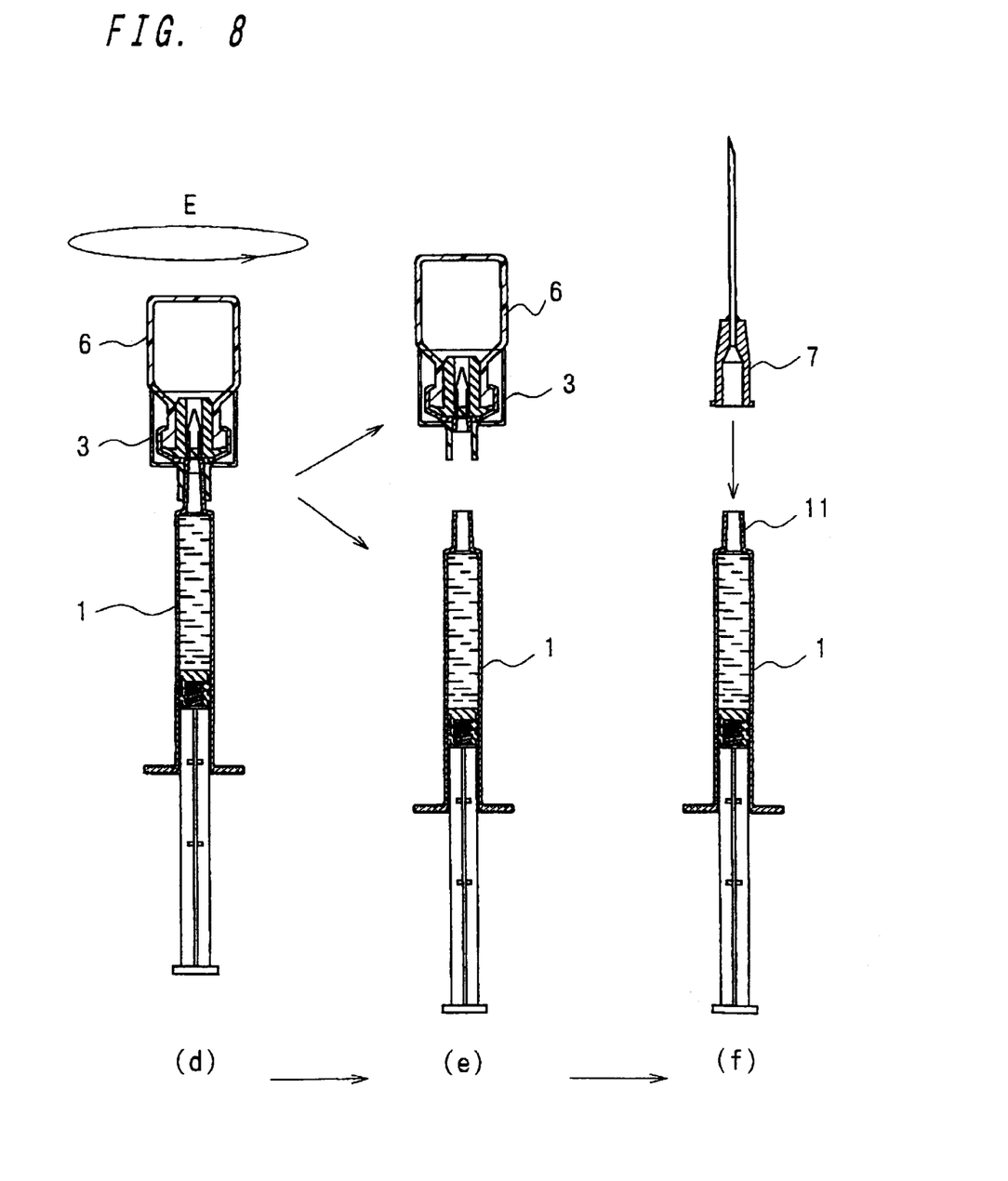

The piercing needle 13 is a hollow needle having a pointed edge 131 at the distal end thereof, and a lumen 132 passing therethrough and communicating with a lumen 112 of the needle-connecting portion 11. The piercing needle 13 is provided, at the proximal portion thereof, i.e., a portion adjacent to the needle-connecting portion 11, with an engaging portion 133 which is adapted to be engaged with an engaging means 321 provided in the fitting portion 32 of the guide means 3 mentioned below. As best shown in FIG. 2, a proximal part of the engaging portion 133 is tapered toward the needle-connecting portion 11 to make the piercing needle 13 easily breakable at the proximal end 135 of the engaging portion 133. Thus, the piercing needle 13 can be easily broken off at the proximal end 135 of the engaging portion 133 by turning the guide means 3 relative to said barrel 1 and then removed from the needle-connecting portion 11 of the barrel 1 together with guide means 3 and the vial 6, as shown in FIG. 8(e). The engaging portion 133 may be made into the shape with a regular polygonal cross-section or the like as illustrated in FIG. 3(a) designated by 134 in FIG. 3(b), or it may be made into a shape with one or more longitudinal ribs provided on an outer wall thereof. The piercing needle 13 may be protected against contamination by a cap 4 fitted thereon, as illustrated in FIG. 1.

Figure 7:
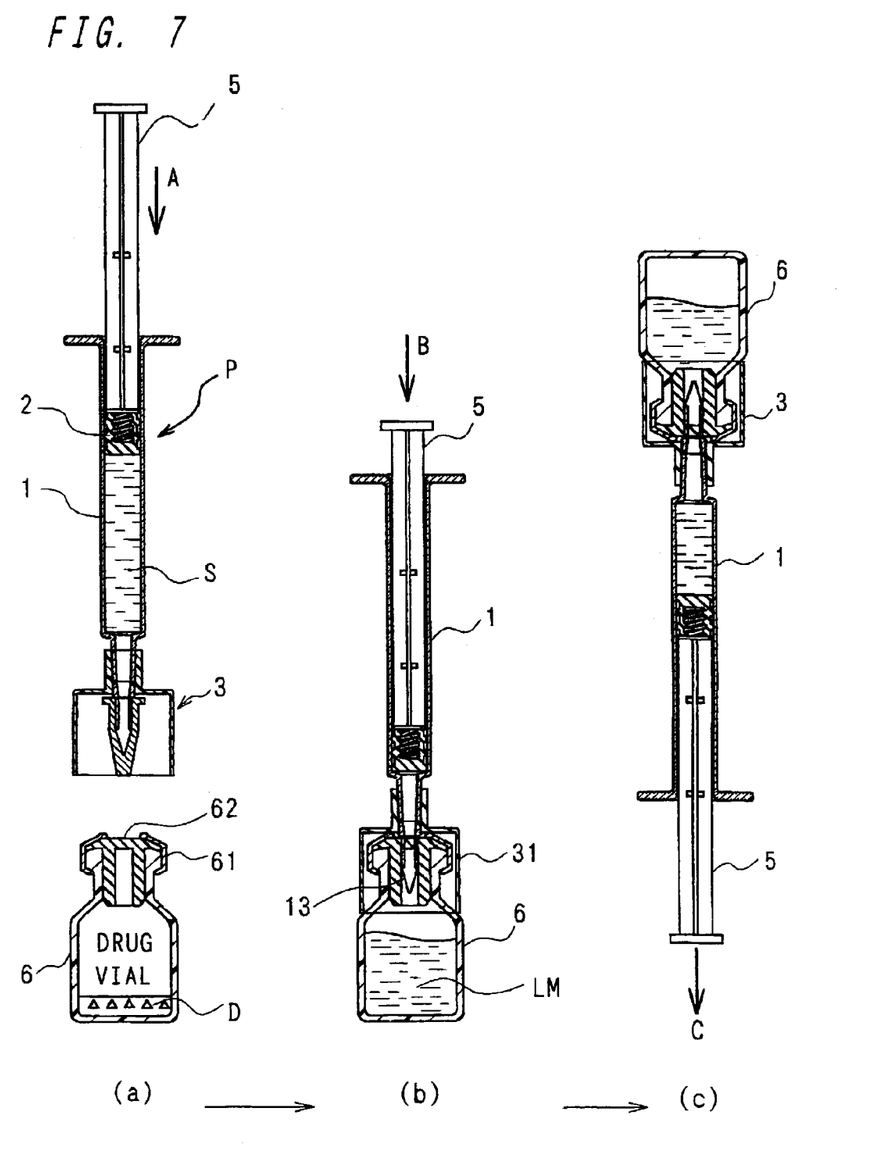
FIGS. 7 and 8 are schematic diagrams illustrating usage of the syringe-type container for liquid medicine according to the present invention.

The gasket 2, made of an elastic material such as butyl rubber or a thermoplastic elastomer, is inserted into the barrel 1 through the proximal open end 12 thereof and liquid-tightly and slidably held in the barrel 1. The gasket 2 is provided at the proximal portion thereof with an engaging means such as an internal thread 21 to associate it with a plunger as illustrated in FIG. 7. The guide means 3 is fitted on the distal side of the needle-connecting portion 11 of the barrel 1 to guide a mouth 61 of a vial (designated by 6 in FIG. 7) along the longitudinal axis of the barrel 1. The guide means 3 is adapted to allow the piercing needle 1 to be broken away from the needle-connecting portion 11 when the guide means 3 is turned relative to the barrel 1.

Figure 4:
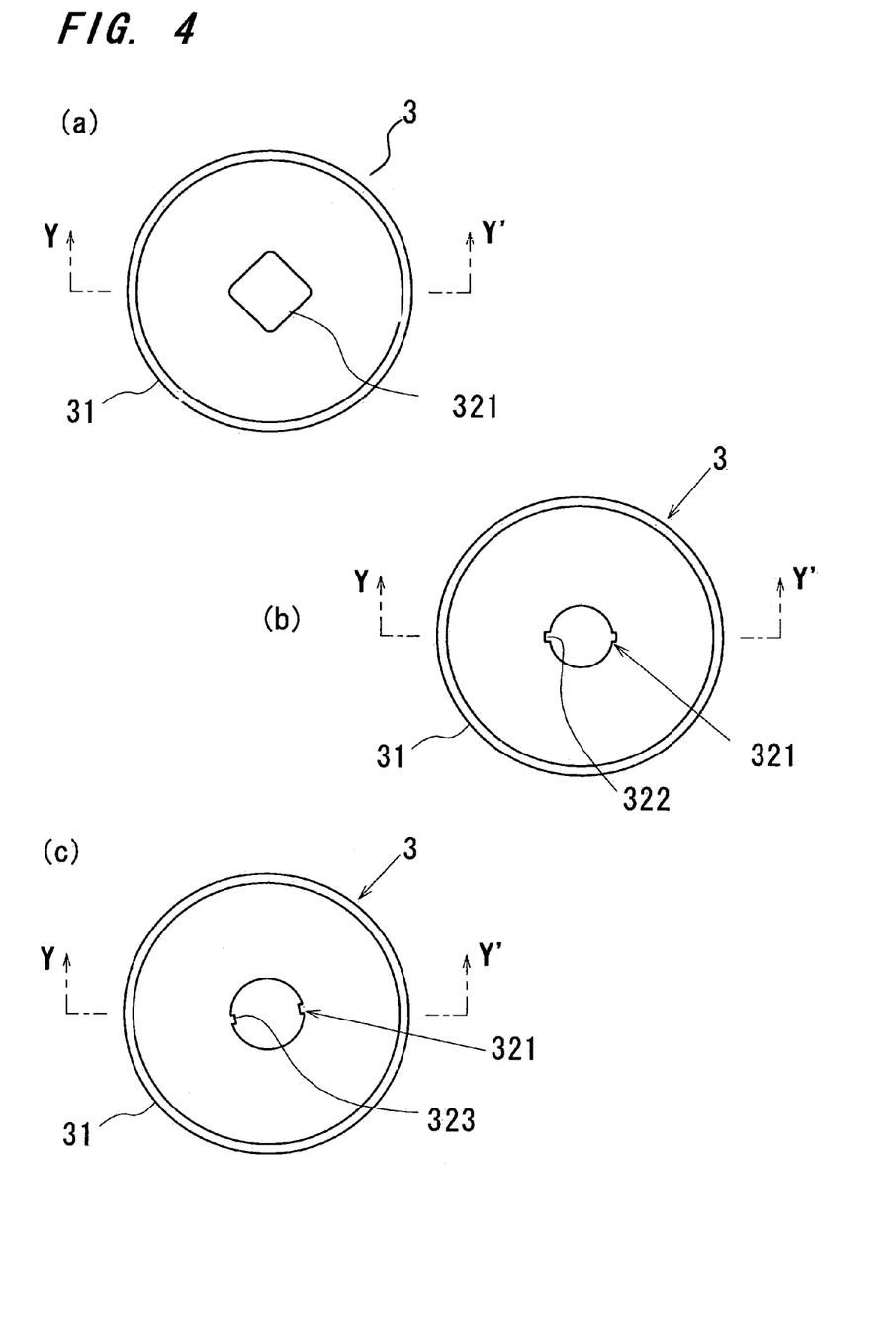
FIG. 4 shows enlarged plan views of the guide means shown in FIG. 1.
Figure 5:
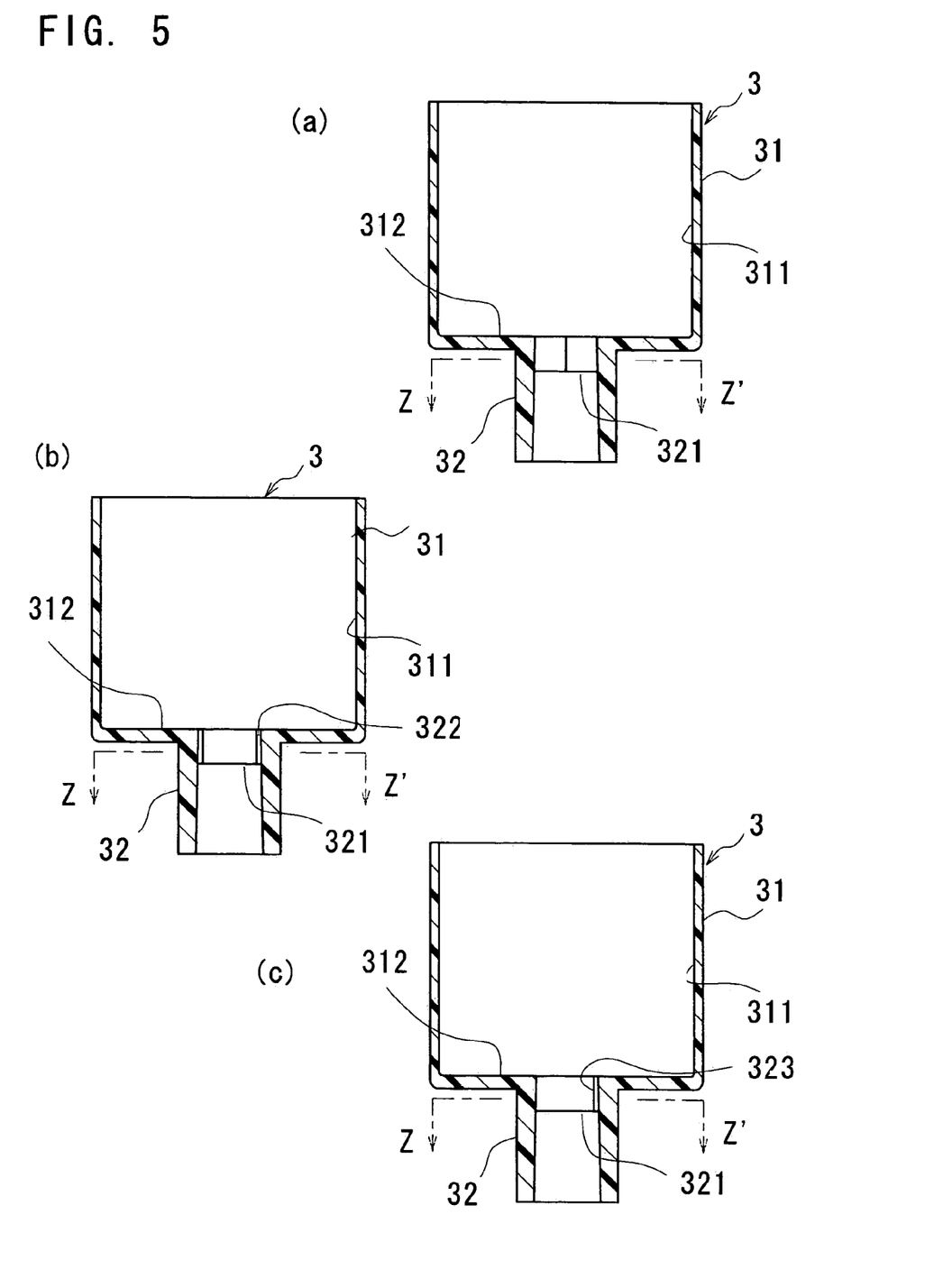
FIG. 5 shows enlarged section views of guide means shown in FIG. 1.
Figure 6:
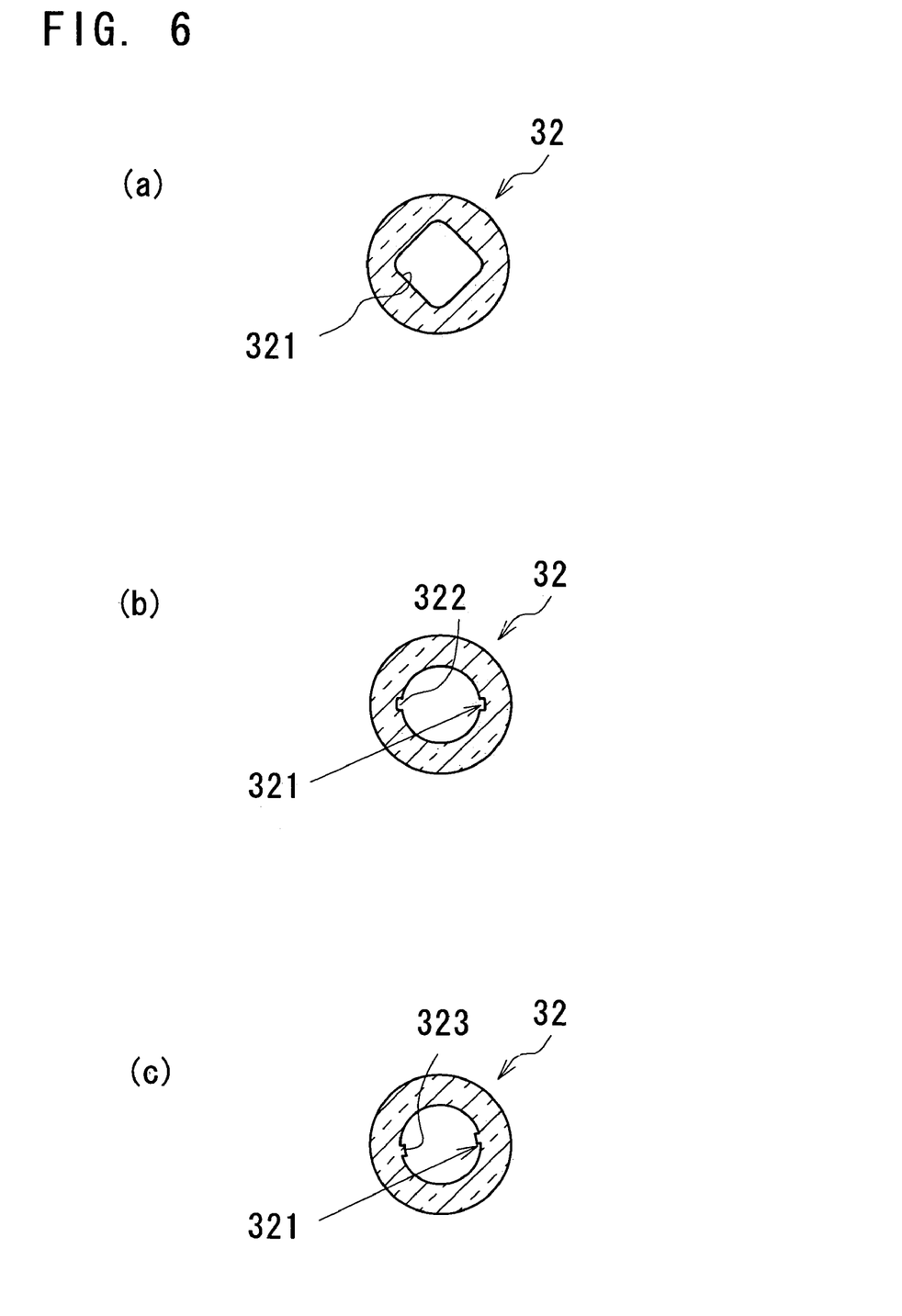
FIG. 6 shows enlarged section views of the guide means shown in FIG. 1.

The guide means 3 is made of a synthetic resin such as polypropylene, ABS resin or polyethylene and includes a guide portion 31 adapted to slidably and removably hold the mouth 61 of the vial 6 inserted therein, and a fitting portion 32 to be fitted on the needle-connecting portion 11, as illustrated in FIGS. 4 to 6. The guide portion 31 is made into a bottom-closed cylindrical shape with an inner diameter approximately equal to the outer diameter of the mouth 61 of the vial 6 so that the vial 6 inserted into the guide means 3 is slidable along the side wall 311 of the guide means 3 in the direction approximately perpendicular to a bottom face 312 of the guide means 3. The fitting portion 32 is so designed as to have a shape in which at least the proximal side is complementary to the shape of the needle-connecting portion 11 to be fitted therein. In other words, the fitting portion 32 is made into a tubular shape with an inner diameter gently tapered toward the distal end thereof. At the distal side of the fitting portion 3, i.e., at a portion adjacent to the guide portion 31, there is provided the engaging means 321 to be engaged with the engaging portion 133 of the piercing needle 13. The engaging means 321 is made into a shape complementary to the engaging portion 133. For example, if the engaging portion 133 is made into a shape with a regular polygonal cross section, the engaging means 321 may be formed as a lumen 321 with a cross section complementary to, as illustrated in FIG. 4(a) the engaging portion 133. If the engaging portion 133 is provided on the outer wall thereof with one or more longitudinal ribs 134, the engaging means 321 may contain one or more longitudinal grooves designed by 322 in FIG. 4(b) adapted to be engaged with the longitudinal ribs designed by 323 in FIG. 4(c), or one or more longitudinal ribs adapted to be engaged with the longitudinal ribs 134 of the engaging portion 133 when the guide means 3 is turned around the axis of the piercing needle 13. In this case, the engaging portion 133 is generally provided with one longitudinal rib, but it may be provided with two or more longitudinal ribs. Although one longitudinal rib used as the engaging means is a sufficient condition, it is preferred to provide a plurality of ribs (preferably, three to five ribs) at even intervals since the use of plural ribs makes it possible to reduce the rotational angle of the guide means 3.

The syringe-type container for liquid medicine according to the present invention may be used as a so-called "prefilled syringe", i.e., a syringe containing a liquid medicine previously charged therein. In this case, the piercing needle 13 on the distal side of the syringe should be closely sealed with a cap 4 of butyl rubber or a thermoplastic elastomer.

The prefilled syringe of the present invention may be used according to the following procedure, which will be explained below with reference to FIGS. 7 and 8. Firstly, after preparing a prefilled syringe P and a vial 6, a plunger 5 is connected to the gasket 2 of the prefilled syringe P, as illustrated in FIG. 7a. After removing the cover 4 from the piercing needle 13, the prefilled-syringe P is moved in the direction of an arrow A and then the rubber stopper 62 of the vial 6 is pierced with the piercing needle 13 as illustrated in FIG. 7b by sliding the mouth 61 of the vial 6 along the guide portion 31 of the guide means 3. The solution S in the barrel 1 of the prefilled-syringe P is injected into the vial 6 by pushing the plunger 5, and then the vial 6 is fully shaken for mixing the solution S with the drug D. The vial 6 and the prefilled syringe P are turned upside down as illustrated in FIG. 7c. By moving the plunger 5 in the direction of an arrow C, the resultant liquid medicine LM in the vial 6 is drawn into the barrel 1 of the prefilled syringe. By turning the vial 6 in the direction of an arrow E as illustrated in FIG. 8d, the piercing needle 13 is broken off and removed together with the guide means 3 and the vial 6 from the prefilled syringe P as illustrated in FIG. 8e. After fitting a needle 7 on the needle-connecting portion 11 of the prefilled syringe P as illustrated in FIG. 8f, by pressing the plunger toward the needle-end, the liquid medicine may be injected into a cavity of the body such as the vein of a patient.

As will be understood from the above, the present invention makes it possible to prepare a liquid medicine without causing any injury of the user and coring of a rubber stopper.

Further, there is no need to separate any metal needle from the plastic members since the syringe-type container of the present invention has no metal needle.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

The invention claimed is:

1. A syringe-type container for housing liquid medicine which comprises:
 a barrel which defines a lumen and has a proximal end and a distal end, said barrel having a needle-connecting portion disposed at said distal end and including an easily breakable piercing needle coaxially formed at a distal end of said needle connecting portion, said piercing needle including an engaging portion which defines a proximal portion of the piercing needle;
 a liquid tight gasket slidably disposed in the barrel to close the lumen of the barrel at said proximal end; and
 a hollow guide means fitted on the needle-connecting portion of said barrel, said guide means having a fitting portion fitted on the needle-connecting portion of said barrel and a cylindrical guide portion for slidably receiving a vial inserted therein, said fitting portion containing an engaging means for engagement with the engaging portion of said piercing needle;
 wherein said barrel, needle-connecting portion, engaging portion and piercing needle are formed in a single piece, and wherein said piercing needle is so formed as to be breakable at a proximal end of said engaging portion, whereby the piercing needle is adapted to be broken off from the needle-connecting portion when said guide means is turned relative to said barrel.

2. The syringe-type container for liquid medicine according to claim 1, wherein said engaging portion of said piercing needle is made into a shape with a regular polygonal cross section, and wherein the engaging means of said fitting portion is a lumen with a cross section complementary to the shape of said engaging portion.

3. The syringe-type container for liquid medicine according to claim 1, wherein the engaging portion of said piercing needle is provided with at least one longitudinal rib, and wherein the engaging means of said fitting portion includes at least one longitudinal groove and adapted to be engaged with said at least one longitudinal rib of said engaging portion.

4. The syringe-type container for liquid medicine according to claim 1, wherein said engaging portion of said piercing needle is provided with at least one longitudinal rib, and wherein the engaging means of said fitting portion includes at least one longitudinal rib which is adapted to engage with said at least one longitudinal rib of the engaging portion when said guide means is turned around the piercing needle.

5. The syringe-type container for liquid medicine according to claim 1, wherein said container is filled with a liquid medicine
 and a cap is fitted on said piercing needle to seal the piercing needle.

6. A prefilled syringe containing a liquid medicine previously charged therein which comprises:
 a barrel which defines a lumen and has a proximal end and a distal end, said barrel having a needle-connecting portion disposed at said distal end and including an easily breakable piercing needle coaxially formed at a distal end of said needle-connecting portion, said piercing needle including an engaging portion which defines a proximal portion of the piercing needle;
 a liquid tight gasket slidably disposed in the barrel to close the lumen of the barrel at said proximal end; and
 a hollow guide means fitted on the needle-connecting portion of said barrel, said guide means having a fitting portion fitted on the needle-connecting portion of said barrel and a cylindrical guide portion for slidably receiving a vial inserted therein, said fitting portion containing an engaging means for engagement with the engaging portion of said piercing needle;
 a cap removably fitted on said piercing needle to close a lumen of said piercing needle at the distal end thereof;
 a liquid medicine disposed in said barrel;
 wherein said barrel, needle-connecting portion, engaging portion and piercing needle are formed in a single piece, and wherein said piercing needle is so formed as to be breakable at a proximal end of said engaging portion, whereby the piercing needle is adapted to be broken off from the needle-connecting portion when said guide means is turned relative to said barrel.

* * * * *